US006776977B2

(12) United States Patent
Liu

(10) Patent No.: US 6,776,977 B2
(45) Date of Patent: Aug. 17, 2004

(54) POLYPODAL CHELANTS FOR METALLOPHARMACEUTICALS

(75) Inventor: Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 2 days.

(21) Appl. No.: 10/033,770

(22) Filed: Dec. 27, 2001

(65) Prior Publication Data

US 2002/0090342 A1 Jul. 11, 2002

Related U.S. Application Data

(60) Provisional application No. 60/260,615, filed on Jan. 9, 2001.

(51) Int. Cl.[7] .......................... A61K 51/00; A61B 5/00; C07F 9/02; A01N 57/10
(52) U.S. Cl. ...................... 424/1.77; 424/9.36; 424/9.4; 558/166; 514/143
(58) Field of Search ...................... 568/8, 17; 424/1.65, 424/9.36, 9.364, 9.365, 1.77, 9.4; 558/166; 514/143

(56) References Cited

U.S. PATENT DOCUMENTS

| | | | |
|---|---|---|---|
| 3,974,268 A | | 8/1976 | Subramanian et al. |
| 4,399,817 A | | 8/1983 | Benedict |
| 4,882,142 A | | 11/1989 | Simon et al. |
| 4,898,724 A | | 2/1990 | Simon et al. |
| 5,206,370 A | | 4/1993 | Schwartz et al. |
| 5,236,695 A | | 8/1993 | Winchell et al. |
| 5,300,279 A | * | 4/1994 | Simon et al. ............... 424/1.77 |
| 5,342,606 A | | 8/1994 | Sherry et al. |
| 5,450,601 A | | 9/1995 | Okuda |
| 5,565,184 A | | 10/1996 | Dunn et al. |
| 5,593,659 A | | 1/1997 | Winchell et al. |
| 5,744,120 A | | 4/1998 | Edwards et al. |
| 6,107,482 A | | 8/2000 | Cook et al. |

FOREIGN PATENT DOCUMENTS

| | | |
|---|---|---|
| EP | 0210043 | 1/1987 |
| EP | 291605 | 5/1987 |
| EP | 441953 B1 | 8/1991 |
| EP | 0468634 | 1/1992 |
| EP | 569132 B1 | 11/1993 |
| WO | WO 92/08725 | 5/1992 |
| WO | WO 94/26754 | 11/1994 |
| WO | WO 95/01124 | 1/1995 |
| WO | WO 95/05118 | 2/1995 |
| WO | WO 9630377 | 10/1996 |
| WO | WO 97/31005 | 8/1997 |

OTHER PUBLICATIONS

Stanley, I. K. et al. *Anticancer Res.* 1988, 8, 681–684.
Dewanjee, M. K. *Semin. Nucl. Med.* 1990, 20, 5.
Liu, et al *Pure & Appl. Chem.* 1991, 63, 427.
Garrett et al., *J. Am. Chem. Soc.* 1991, 113, 2965–2977.
Tor, Y., et al. *J. Am. Chem. Soc.* 1992, *114*,6653–6661.
Griffiths et al., *Bioconj. Chem.* 1992, *3*, 91.
Liu, S., et al. *J. Am. Chem.Soc.* 1992, *114*, 6081.
Tor et al. *J. Am. Chem Soc.* 1992, 6661–6671.
Stack et al., *J. Am. Chem Soc.* 1992, 114, 1512–1514.
Liu, S., et al. *Inorg. Chem.* 1993, *32*, 2773.
Liu, S., et al. *Inorg. Chem.* 1993, *32*, 4268.
Liu, S., et al. *Inorg. Chem.* 1993, *32*, 1756.
Karpishin, T. B., et al *J. Am. Chem. Soc.* 1993, *115*, 182–192.
Karpishin, T. B., et al. *J. Am. Chem. Soc.* 1993, *115*, 6115–6125.
Silberstein, E. B. *Semin. Oncol.* 1993, *20*, 10–20.
Ackey, D. and Yardly, J. *Semin. Oncol.* 1993, 20 (suppl.), 27–31.
Dayan, I., et al. *Inorg. Chem.* 1993, *32*, 1467–1475.
Yakirevitch, P., et al. *Inorg. Chem.* 1993, *32*, 1779–1787.
Jurisson, et al *Chem. Rev.* 1993, *93*, 1137.
Serafini, A. N. *J. Radiation Oncol. Biol. Phys.* 1994, *30*, 1187–1194.
Carvan, P., et al. *J. Am. Chem. Soc.* 1995, *117*, 11230–11238.
Yang, L–W. et al. *Inorg. Chem.* 1995, *34*, 4921–4925.
Hom et al., *Nucl. Med. Biol.* 1997, 24, 485.
Liu, et al *Bioconj. Chem.* 1997, *8*, 621.
McEwan, A. J. B. *Semin. Nucl. Med.* 1997, *27*, 165–182.
Liu, S., et al. *Bioconjugate Chem.* 1997, *8*, 621–636.
Meyer, M., et al. *J. Am. Chem. Soc.* 1197, *119*, 10093–10103.
P. Kong Thoo Lin et al., Synthesis, Jun. 1998, 859–866.
Dilworth, J. R. and Parrott, S. J. *Chem. Soc. Rev.* 1998, *27*, 43.
Kuksa et al, Synthesis 1999, 6, 1034–1038.
Liu, S. and Edwards, D. S. *Chem. Rev.* 1999, *99*, 2235–2268.
Jurisson, S. and Lydon, J. D. *Chem. Rev.* 1999, *99*, 2205–2218.
Anderson, C. J. and Welch, M. J. *Chem. Rev.* 1999, *99*, 2219–2234.
Volkert, W. A. and Hoffman, t. J. *Chem. Rev.* 1999, *99*, 2269–2292.
Caravan, P. et al. *Chem. Rev.* 1999, *99*, 2293–2352.
*Chem. Commum.* 1999, 457–458.
Runge, V. M. *J. Magn. Reson. Imaging*2000, *12*, 205–213.
Bouchet, L. G., et al. *J. Nucl. Med.* 2000, *41*, 682–687.
Krishnamurthy, G. T. and Krishnamurthy, S. *J. Nucl. Med.* 2000, *41*, 688–691.

* cited by examiner

*Primary Examiner*—Michael G. Hartley
(74) *Attorney, Agent, or Firm*—Warren K. Volles; Woodcock Washburn LLP

(57) ABSTRACT

Tripodal polyaminophosphonate chelants are disclosed, as well as chelates of the chelants with metal ions to form radiopharmaceutical and radioactive, MRI and X-ray or CT imaging compounds and compositions. Therapeutic and imaging methods of use are also disclosed.

3 Claims, No Drawings

POLYPODAL CHELANTS FOR METALLOPHARMACEUTICALS

FIELD OF THE INVENTION

This invention relates to a novel class of tripodal polyaminophosphonates and metal chelates thereof, methods of preparing the tripodal polyaminophosphonate chelants and metal complexes, and pharmaceutical compositions comprising the tripodal polyaminophosphonate chelants and metal chelates. This invention relates particularly to the use of the new metal chelates as contrast agents for x-ray or MRI imaging. This invention also relates to the use of metal chelates useful as diagnostic radiopharmaceuticals for imaging the skeleton, myocardial infarction, infarctions of the spleen and bowel, inflammatory bowel disease, radiation injury, metastastic calcification, bone cancer, and various bone disorders. This invention also relates to the use of radiometal chelates particularly useful as therapeutic radiopharmaceuticals for bone pain relief, bone marrow suppression, the treatment of bone cancer, and various bone disorders.

BACKGROUND OF THE INVENTION

The development of a bone metastasis is a common and often catastrophic event for a cancer patient. The number of patients with metastastic disease is large among those who have breast cancer, prostate cancer, and lung carcinoma, as well as other tumors (Bouchet, L. G., et al. *J. Nucl. Med.* 2000, 41, 682–687). The pain, pathological fractures, frequent neurological deficits and forced immobility caused by these metastastic lesions significantly decreases the quality of life for cancer patient. The initial goal for the treatment is to relieve the pain, reduce narcotic medication requirement, and increase ambulation.

The use of radionuclides for the treatment of metastastic cancer started in the early 1950's. It has been proposed that a radionuclide, particularly □-emitters, could be concentrated in the fast growing portion of the bone with minimal amounts of radiation reaching the soft tissue or normal bone. Over the years, treatment of bone pain using bone-seeking radiopharmaceuticals has been explored extensively. The use of radiopharmaceuticals which cause partial or total suppression or eradication of the bone marrow has become an accepted part of procedures used to treat a patients with cancer such as leukemias, lymphomas, myelomas and Hodgkin's disease as well as in the treatment of patients suffering from genetic disorders such as sickle cell anemia and thalassemia. Details on the use of therapeutic radiopharmaceuticals for bone pain palliation and treatment of bone metastases can be found in the following references: Stanley, I. K. et al. *Anticancer Res.* 1988, 8, 681–684; Serafini, A. N. *J. Radiation Oncol. Biol. Phys.* 1994, 30, 1187–1194; McEwan, A. J. B. *Semin. Nucl. Med.* 1997, 27, 165–182; Krishnamurthy, G. T. and Krishnamurthy, S. *J. Nucl. Med.* 2000, 41, 688–691; Bouchet, L. G., et al. *J. Nucl. Med.* 2000, 41, 682–687.

$^{32}$P-labeled orthophosphate (Silberstein, E. B. *Semin. Oncol.* 1993, 20, 10–20) and $^{89}$SrCl$_3$ (Ackey, D. and Yardly, J. *Semin. Oncol.* 1993, 20 (suppl.), 27–31) are the first radiopharmaceuticals to be evaluated for this purpose. U.S. Pat. No. 4,399,817 discloses the use of phosphorus compounds containing a boron residue. The compounds were injected into the body and accumulated in the skeletal system. The patient was then irradiated with neutrons in order to activate the boron, and to give a radiation dose.

The drawback associated with $^{32}$P and $^{89}$Sr as palliative agents is that both isotopes are high-energy □-emitters with very long penetration range, which can result in significant irradiation of the marrow compartment and depression of normal bone function. Therefore, it is impossible to give therapeutic doses to the tumor without substantial damage to normal bone and soft tissues.

Polyaminophosphonate chelants show very high affinity for hard cations such as $Ca^{2+}$ and lanthanide metal ions. Metal chelates of polyaminophosphonates often localize in bone in a short period of time, probably in part due to interactions of the uncoordinated oxygen donors in the polyaminophosphonate chelate with $Ca^{2+}$ on the bone surface. Due to their high bone uptake, radiometal chelates of polyaminophosphonate chelants have been studied as therapeutic radiopharmaceuticals for bone-pain palliation and for the treatment of bone cancer metastasis. European patent application No. 291,605 and U.S. Pat. No. 4,898,724 disclose the use of Sm-153, Gd-159, or Ho-166 chelates for bone marrow suppression. The lanthanide chelate contains a linear polyaminophosphonate chelant selected from ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), or tris(2-aminoethyl)aminehexamethylenephosphonic acid (TTHMP). U.S. Pat. No. 4,882,142 discloses the use of Sm-153, Gd-159, or Ho-166 chelates with 1,4,7,10-tetraazacyclododecanetetramethylenephosphonic acid (DOTMP) for bone marrow suppression and other bone-related diseases. The chelate $^{153}$Sm-EDTMP (Quadramet®) has recently been approved by FDA for bone pain palliation. The chelate $^{166}$Ho-DOTMP is under clinical investigation for both bone pain palliation and the treatment of bone metastases. Despite their success, there is still a need for a better therapeutic radiopharmaceutical labeled with an appropriate lanthanide radionuclide.

Prior to therapy it is necessary to obtain reliable diagnostic information and to this end several approaches have been tried. It is known that phosphates and phosphonates have an affinity for hydroxyapatite crystals, and tend to localize in vivo in the regions of bone metabolism, and in certain tumors, such as neuroblastoma. The uptake of radiopharmaceuticals containing phosphonate chelant in tumors is attributed to calcification in tumors. For example, U.S. Pat. No. 3,974,268 discloses the use of technetium-99m ($^{99m}$Tc) chelates of diphosphonate chelants as skeletal imaging agents. The diphosphonate is used as both the bone targeting-agent and the chelating agent for $^{99m}$Tc. The properties of these radiopharmaceuticals, which lead to their localization in bone, also allow for them to localize in soft tissues bearing recognition features in common with bone. Localization of such agents in areas of myocardial infarction is an example of one application, which has proven diagnostically useful. Radiopharmaceuticals, which localize in bone, also have been shown to localize infarctions of the spleen and bowel, inflammatory bowel disease, radiation injury, as well as metastastic calcification.

Radionuclides, including but not limited to $^{99m}$Tc, $^{117m}$Sn, $^{111}$In, $^{67}$Ga, $^{68}$Ga, $^{89}$Zr, $^{62}$Cu, $^{64}$Cu and $^{67}$Cu, have been proposed for diagnostic imaging. The choice of the radionuclide depends largely on the physical and nuclear properties (half-life and □-energy), availability, and cost. In general, generator-produced radionuclides are considered ideal, since the generator system consists of a long-lived parent isotope that decays to a short-lived daughter isotope. The daughter can be easily separated from the parent by either ion-exchange chromatography or solvent extraction.

Nearly 80% of radiopharmaceuticals used in nuclear medicine are $^{99m}$Tc-labeled compounds. The reason for such a preeminent position of $^{99}$mTc in clinical use is its extremely favorable physical and nuclear characteristics. The 6 h half-life is long enough to carry out radiopharmaceutical synthesis and to collect useful images. At the same time, it is short enough to permit the administration of millicurie amounts of $^{99m}$Tc radioactivity without significant radiation dose to the patient. The monochromatic 140 KeV photons are readily collimated to give images of superior spatial resolution. Furthermore, $^{99m}$Tc is readily available from commercial $^{99}$Mo—$^{99m}$Tc generators at low cost.

Various $^{99m}$Tc-labeling techniques have been described in several reviews (Liu, S. and Edwards, D. S. Chem. Rev. 1999, 99, 2235–2268; Jurisson, S. and Lydon, J. D. Chem. Rev. 1999, 99, 2205–2218; Anderson, C. J. and Welch, M. J. Chem. Rev. 1999, 99, 2219–2234; Volkert, W. A. and Hoffman, T. J. Chem. Rev. 1999, 99, 2269–2292; Liu, S., et al. Bioconjugate Chem. 1997, 8, 621–636). After radiolabeling, the resulting reaction mixture may optionally be purified using one or more chromatographic methods, such as Sep-Pack or high performance liquid-chromatography (HPLC). The preferred radiolabeling procedures are those, in which the chelation can be achieved without post-labeling purification.

Nuclear magnetic resonance (NMR) is based on the absorption of radio-frequency energy by the magnetic moment of atomic nuclei in samples placed in a strong magnetic field. Conventional magnetic resonance imaging (MRI) of human body relies mainly on the detection of most abundant type of nuclei, the hydrogen in water (and to some extent, fat). For discrimination of healthy and diseased tissues, adequate contrast is essential. Such contrast depends not only on differences in water concentration, but also on the NMR relaxation times $T_1$ and $T_2$, which in turn are related to local mobility and interactions. The MRI contrast agent is used to improve diagnosis of disease by changing tissue signal intensity. Contrast agents increase both $1/T_1$ and $1/T_2$ to varying degrees depending on their nature as well as the applied magnetic field. Agents such as gadolinium(III) that increase $1/T_1$ and $1/T_2$ by roughly similar amounts are best visualized using $T_1$-weighted images since the percentage change in $1/T_1$ in tissue is much greater than that in $1/T_1$ (Caravan, P. et al. Chem. Rev. 1999, 99, 2293–2352). Iron-oxide particles generally lead to a much larger increase in $1/T_2$ than in $1/T_1$ and are best seen with in $T_2$-weighted scans.

MRI diagnosis has become a widely accepted diagnostic modality for a variety of diseases. The availability of MRI devices has led to the use of MRI in medical examination for the detection and diagnosis of disease states and other internal abnormality. The continued use and rapid development of MRI has stimulated interest in the development of new MRI contrast agents. Most of MRI contrast agents commercially available or under clinical investigations are metal chelates containing paramagnetic metal ions, such as $Fe^{3+}$, $Gd^{3+}$, $Mn^{2+}$, and $Cu^{2+}$. When compared to other contrast agents, the MRI contrast agents provide superior spatial resolution in tissues, and are safe due to the absence of exposure to X-rays or gamma radiation. The metal chelates have proved to be exceptionally well-tolerated class of contrast media. In particular, gadolinium MRI contrast agents do not show any nephrotoxicity in contrast to iodinated contrast media for CT (Runge, V. M. J. Magn. Reson. Imaging 2000, 12, 205–213).

Agents, which localize in bone and which provide MRI contrast enhancement, could be used to perform similar diagnostic procedures employing radiopharmaceuticals which localize in bone. Given the substantially greater spatial and temporal resolution of MRI techniques, as compared to nuclear medicine procedures, it is anticipated that useful diagnostic information could be obtained in abnormalities which were be able to be detected using radiopharmaceutical agents. The major difference between radiopharmaceuticals and MRI contrast agents is that radiopharmaceuticals are administered in very small dose and there is little need to minimize the toxicity of these agents while MRI contrast agents are administered in relatively large quantities and it is often desirable to reduce the toxicity by maximizing water solubility.

Art in the MRI field is quite extensive, such that the following summary, not intended to be exhaustive, is provided only as references. Discussions of metal chelates of polyaminophosphonates as MRI contrast agents are found in U.S. Pat. Nos. 5,593,659, 5,342,606, 5,236,695, PCT patent application WO 97/31005, PCT patent application WO 95/05118, PCT patent application WO 94/26754, PCT patent application WO 92/08725, European patent application No.0468634, and European patent application No.0210043. Functional tripodal chelants and the use of their metal chelates in MRI imaging, x-ray imaging, and scintigraphic imaging are disclosed in PCT patent application No. WO 95/01124, U.S. Pat. Nos. 5,565,184 and 5,450,601.

There is a continuing need for new and structurally diverse chelants and their metal chelants for use as MRI contrast agents or therapeutic radiopharmaceuticals for bone marrow suppression, bone pain relief, the treatment of bone cancer, and various bone disorders. There is also a further need to develop highly stable metal chelates with good relaxicity and osmolar characteristics.

Polydentate chelants with three-dimensional cavities are of great interest because of the high stability of the metal chelates, the substantial selectivity for certain metal ions, either by enforcing a specific spatial arrangement of donor atoms or by introducing different donor atoms into the ligand backbone, and their capability to adopt a preorganized conformation in the unchelated form. The higher the degree of preorganization of an unchelated ligand, the more stable the complex is.

Preorganization minimizes the freedom of motion of the donor atoms and the chelant framework during the complexation process in such a way that the free ligand has a conformation more similar to that in the complex. Because of the restricted freedom of motion, the loss of entropy in forming the complex is much less, which leads to the increased thermodynamic stability of the metal chelate. Although preorganization is a concept usually applied to macrocyclic and cryptate metal complexes, it is also of some importance for open-chain chelants. For example, metal complexes of CDTA (trans-cyclohexane-diaminetetraacetic acid) are often 2–3 orders of magnitude more stable than those of EDTA (ethylenediamine-tetraacetic acid) because of the restricted motion of the iminodiacetic chelating arms in CDTA.

Preorganization of a polydentate chelator results in not only high thermodynamic stability but also increased kinetic inertness of its metal chelate. This has been exemplified by the fact that the half-life for Gd(DOTA)$^-$ in 0.1 M HCl is 60.2 h and 2000 years at pH=6.0 while the complex Gd(DTPA)$^{2-}$ having comparable thermodynamic stability decomposes rapidly under acidic conditions ($K_{obs}$=1.2×10$^{-3}$ s$^{-1}$; $t_{1/2}$~1 min). The highly preorganized macrocyclic framework of DOTA forces four aminoacetate chelating arms to adopt a conformation that the metal ion can be wrapped in an $N_4O_4$ donor set. At the same, it is more difficult for the coordinated acetate to be dissociated from the metal center.

There are several ways to achieve a high degree of preorganization for a polydentate chelant. These include the use of a macrocyclic ligand framework, the use of hydrogen bond(s) to enforce a three dimensional cavity for metal coordination, and the choice of chelating arms. Poly aminocarboxylate ligands based on cyclen are known to be well preorganized and form highly stable lanthanide complexes due to the endocyclic orientation of the nitrogen donors. The siderophore enterobactin forms much more stable $Fe^{3+}$ complex than MECAM does because of the cyclic triester framework and hydrogen bonding (Garrett, T. M., et al. *J. Am. Chem. Soc.* 1991, 113, 2965–2977; Stack, T. D. P., et al. *J. Am. Chem. Soc.* 1992, 114, 1512–1514; Tor, Y., et al. *J. Am. Chem. Soc.* 1992, 114, 6661–6671; Karpishin, T. B., et al *J. Am. Chem. Soc.* 1993, 115, 182–192; Karpishin, T. B., et al. *J. Am. Chem. Soc.* 1993, 115, 6115–6125; Meyer, M., et al. *J. Am. Chem. Soc.* 1997, 119, 10093–10103.). Tripodal peptides with chiral conformations were found to be stabilized by interstrand hydrogen bonds (Yakirevitch, P., et al. *Inorg. Chem.* 1993, 32, 1779–1787; Dayan, I., et al. *Inorg. Chem.* 1993, 32, 1467–1475; Tor, Y., et al. *J. Am. Chem. Soc.* 1992, 114,6653–6661.). It was also found that hydrogen bonding plays a significant role in the conformation of the uncoordinated tripodal aminephenol ligands (Caravan, P., et al. *J. Am. Chem. Soc.* 1995, 117, 11230–11238; Yang, L-W., et al. *Inorg. Chem.* 1995, 34, 4921–4925; Liu, S., et al. *Inorg. Chem.* 1993, 32, 4268; Liu, S., et al. *Inorg. Chem.* 1993, 32, 2773; Liu, S., et al. *Inorg. Chem.* 1993, 32, 1756; Liu, S., et al. *Inorg. Chem.* 1992, 31, 5400; Liu, S., et al. *J. Am. Chem. Soc.* 1992, 114, 6081.) The use of a carbon atom as the bridgehead instead of a tertiary nitrogen atom also limits the motion of the aminephenol chelating arms. Renaud, et al (*Chem. Commum.* 1999, 457–458) reported $C_3$ symmetrical lanthanide podates organized by intramolecular trifurcated hydrogen bonds.

What really makes the new chelants described in this invention unique is that the tripodal polyaminophosphonate chelant contains three chelating arms, each of which contains three donor atoms (for example: amine-N, phenolate-O or pyridine-N, and phosphonate-O). As a result, they are expected to form stable metal chelates with lanthanide metal ions, such as $Y^{3+}$, $Sm^{3+}$, $Gd^{3+}$, $Dy^{3+}$, $Ho^{3+}$, $Yb^{3+}$, and $Lu^{3+}$. Various spacers or bridging atoms are used to alter the degree of preorganization, thereby the thermodynamic stability and kinetic inertness of their metal chelates.

SUMMARY OF THE INVENTION

This invention relates to a novel class of tripodal polyaminophosphonates and metal chelates thereof, methods of preparing the tripodal polyaminophosphonate chelants and metal complexes, and pharmaceutical compositions comprising the tripodal polyaminophosphonate chelants and metal chelates. This invention relates particularly to the use of the new metal chelates as contrast agents for x-ray or MRI imaging. This invention also relates to the use of metal chelates useful as diagnostic radiopharmaceuticals for imaging the skeleton, myocardial infarction, infarctions of the spleen and bowel, inflammatory bowel disease, radiation injury, metastastic calcification, bone cancer, and various bone disorders. This invention also relates to the use of radiometal chelates particularly useful as therapeutic radiopharmaceuticals for bone pain relief, bone marrow suppression, the treatment of bone cancer, and various bone disorders.

According to one embodiment of the present invention a tripodal polyaminophosphonate chelant is provided, having the formula:

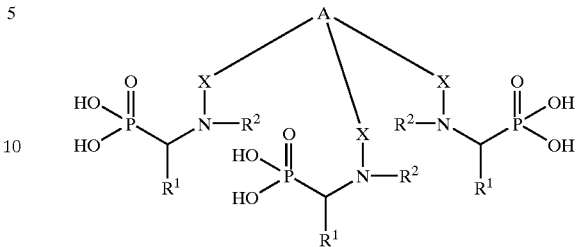

and pharmaceutically acceptable salts thereof,
wherein
A is selected from: $CR^3$, $SiR^3$, $GeR^3$, N, P, P=O, P=S, As, As=O and a macrocyclic group having the formula:

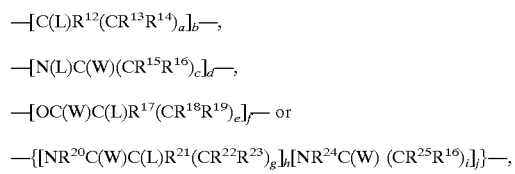

wherein a is an integer selected from 1 to 3;
b is an integer selected from 3 to 5;
c is an integer selected from 1 to 3;
d is an integer selected from 3 or 4;
e is an integer selected from 1 to 3;
f is an integer selected from 3 or 4;
g is an integer selected from 1 to 3;
h is an integer selected from 3 or 4;
i is an integer selected from 1 to 3;
j is an integer selected from 0 to 3;
L is a direct bond to X;
W is $H_2$ or O;
$R^1$ is $(CR^4R^5)_nR^6$, wherein
n is an integer selected from: 0 to 3;
$R^2$, $R^3$, $R^4$, $R^5$, and $R^6$ are independently selected from: H, $C_1$–$C_{10}$ alkyl substituted with 0–5 $R^7$, $C_1$–$C_{10}$ fluoroalkyl substituted with 0–5 $R^7$, $C_2$–$C_{10}$ alkenyl substituted with 0–5 $R^7$, $C_2$–$C_{10}$ fluoroalkenyl substituted with 0–5 $R^7$, aryl substituted with 0–5 $R^7$ and fluroaryl substituted with 0–5 $R^7$; or $R^4$ and $R^5$ may be taken together to form a $C_3$–$C_{10}$ cycloalkyl or $C_3$–$C_{10}$ cycloalkenyl optionally interrupted with C(O)NH, NH, NHC(O), NHC(O)NH, NHC(S)NH, O, S, S(O), $S(O)_2$, P(O) $(OR^8)$, P(O) $(OR^8)O$ or P(O) $(NHR^7)$ O, or aryl or fluoroaryl substituted with 0–5 $R^7$;
$R^7$ is selected from: H, OH, $C(=O)R^8$, $C(=O)OR^8$, $C(=O)NR^8_2$, $PO(OR^8)_2$ and $S(O)_2OR^8$;
$R^8$ is selected from: H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkyl, $C_1$–$C_6$ fluoroalkenyl, benzyl, fluorobenzyl, phenyl and fluorophenyl;
X is selected from: $(CR^9R^{10})_m$, $NR^{11}$ or $O(CR^9R^{10})_m$, wherein m is an integer selected from 1 to 3, provided that when A is N or $-[N(L)C(W)(CR^{15}R^{16})_c]_d-$, X is $(CR^9R^{10})_m$;
$R^9$, $R^{10}$ and $R^{11}$ are independently selected from: H or $C_1$–$C_{10}$ alkyl substituted with 0–5 $R^7$, $C_1$–$C_{10}$ fluoroalkyl substituted with 0–5 $R^7$, $C_2$–$C_{10}$ alkenyl substituted with 0–5 $R^7$, $C_2$–$C_{10}$ fluoroalkenyl substituted with 0–5 $R^7$, aryl substituted with 0–5 $R^7$, fluoroaryl substituted with 0–5 $R^7$; or $R^9$ and $R^{10}$ may be taken together to form a $C_3$–$C_{10}$ cycloalkyl or $C_3$–$C_{10}$ cycloalkenyl optionally interrupted with C(O)NH, NH, NHC(O), NHC(O)NH, NHC(S)NH, O, S, S(O), S(O)$_2$, P(O) (OR$^8$), P(O) (OR$^7$)O, P(O) (NHR$^7$)O or aryl or fluoroaryl substituted with 0–5 R$^8$; and $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ are independently selected at each occurrence from H, $C_1$–$C_6$ alkyl, $C_3$–$C_6$ cycloalkyl, $C_1$–$C_6$ fluoroalkyl, $C_1$–$C_6$ alkenyl, $C_3$–$C_6$ cycloalkenyl, $C_1$–$C_6$ fluoroalkenyl, benzyl, fluorobenzyl, phenyl and fluorophenyl.

According to another embodiment of the present invention, a radiopharmaceutical compound is provided, in which the tripodal polyaminophosphonate chelant of the present invention is chelated with a radionuclide selected from: $^{60}$Cu, $^{62}$Cu, $^{64}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re and $^{188}$Re.

According to another embodiment of the present invention, an MRI contrast agent is provided, in which the tripodal polyaminophosphonate chelant of the present invention is chelated with a paramagnetic metal ion of atomic number 21–29, 42–44 or 58–70.

According to another embodiment of the present invention, an X-ray or CT contrast agent is provided, in which the tripodal polyaminophosphonate chelant of the present invention is chelated with a heavy metal ion of atomic number 21–31, 39–49, 50, 56–80, 82, 83 or 90.

According to another embodiment of the present invention, pharmaceutical compositions are provided for treating bone disorders that benefit from the delivery of cytotoxic doses of radiation in a patient in need thereof, containing the radiopharmaceutical compounds of the present invention and a pharmaceutically acceptable carrier. In yet another embodiment of the present invention treatment methods are provided for treating bone disorders that benefit from the delivery of cytotoxic doses of radiation in a patient in need thereof, in which an effective amount of the aforesaid pharmaceutical composition is administered to the patient. In particular, the pharmaceutical compositions of the present invention may be used to relieve bone pain, suppress bone marrow and treat bone cancer, both primary and metastastic.

According to another embodiment of the present invention, radioactive imaging compositions are provided containing the radiopharmaceutical compounds of the present invention and a pharmaceutically acceptable carrier. In yet another embodiment of the present invention, methods for radioactive imaging are provided in which an effective amount of the radioactive imaging compositions of the present invention are administered to a patient to be imaged sufficiently in advance thereto. The radioactive imaging compositions are, among other things, useful for diagnosis of bone metastases, bone disorders, myocardial infarction, infarctions of the spleen and bowel, inflammatory bowel disease, radiation injury and metastastic calcification.

According to another embodiment of the present invention, magnetic resonance imaging compositions are provided containing the magnetic resonance imaging compounds of the present invention and a pharmaceutically acceptable carrier. In yet another embodiment of the present invention, methods for magnetic resonance imaging are provided in which an effective amount of the magnetic resonance imaging compositions of the present invention are administered to a patient to be imaged sufficiently in advance thereto. The magnetic resonance imaging compositions are, among other things, useful for diagnosis of bone metastases, bone disorders, myocardial infarction, infarctions of the spleen and bowel, inflammatory bowel disease, radiation injury and metastastic calcification.

According to another embodiment of the present invention, X-ray and CT imaging compositions are provided containing the X-ray and CT imaging compounds of the present invention and a pharmaceutically acceptable carrier. In yet another embodiment of the present invention, methods for X-ray and CT imaging are provided in which an effective amount of the X-ray or CT imaging compositions of the present invention are administered to a patient to be imaged sufficiently in advance thereto. The X-ray and CT imaging compositions are, among other things, useful for diagnosis of bone metastases, bone disorders, myocardial infarction, infarctions of the spleen and bowel, inflammatory bowel disease, radiation injury and metastastic calcification.

According to another embodiment of the present invention, compositions for treating heavy metal toxicity in a patient in need thereof are provided containing the polypodal chelant of the present invention and a pharmaceutically acceptable carrier. In yet another embodiment of the present invention, methods for treating heavy metal toxicity in a patient in need thereof are provided in which an effective amount of the aforesaid compositions of the present invention are administered to the patient.

Another embodiment of the present invention is diagnostic kits for the preparation of radiopharmaceuticals or radioactive, magnetic resonance, X-ray or CT imaging agents. Diagnostic kits of the present invention comprise one or more vials containing the sterile, non-pyrogenic, formulation comprised of a predetermined amount of a compound of the present invention, and optionally other components such as one or two ancillary ligands, reducing agents, transfer ligands, buffers, lyophilization aids, stabilization aids, solubilization aids and bacteriostats. The inclusion of one or more optional components in the formulation will frequently improve the ease of synthesis of the radiopharmaceutical by the practicing end user, the ease of manufacturing the kit, the shelf-life of the kit, or the stability and shelf-life of the radiopharmaceutical. The one or more vials that contain all or part of the formulation can independently be in the form of a sterile solution or a lyophilized solid.

DETAILED DESCRIPTION OF THE INVENTION

Tripodal polyaminophosphonate chelants according to the present invention have the formula:

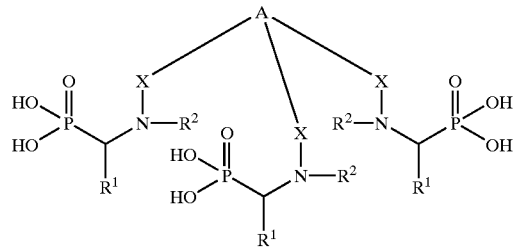

wherein A, X, $R^1$ and $R^2$ have the above-defined values. The spacer, A, is preferably $CR^3$, N and P=O, with $R^3$ having the above-defined values. More preferably, A is $CR^3$ or N, and most preferably N.

$R^1$ is preferably $(CH_2)_nR^6$, with n preferably being 0 or 1. $R^2$, $R^3$ and $R^6$ are preferably independently selected from H, $C_1$–$C_{10}$ alkyl substituted with 0–2 $R^7$, $C_1$–$C_{10}$ fluoroalkyl substituted with 0–2 $R^7$, $C_2$–$C_{10}$ alkenyl substituted with 0–2 $R^7$ $C_2$–$C_{10}$ fluoroalkenyl substituted with 0–2 $R^7$, aryl substituted with 0–2 $R^7$, fluoroaryl substituted with 0–2 $R^7$ and heteroaryl substituted with 0–2 $R^7$. More preferably, $R^2$ and $R^3$ are independently selected from H, $C_1$–$C_{10}$ alkyl, $C_1$–$C_{10}$ fluoroalkyl, $C_2$–$C_{10}$ alkenyl, $C_2$–$C_{10}$ fluoroalkenyl, aryl and fluroaryl; and $R^6$ is an aryl or heteroaryl group substituted with 0–2 $R^7$. Even more preferably, $R^2$ is H and $R^3$ is selected from H, $C_1$–$C_{10}$ alkyl and $C_1$–$C_{10}$ aryl.

$R^7$ is preferably selected from H, OH, C(=O)OH, C(=O)NH$_2$, PO(OH)$_2$ and S(O)$_2$OH. More preferably, $R^7$ is selected from H, OH, C(=O)OH, PO(OH)$_2$ and S(O)$_2$OH.

X is preferably selected from (CH$_2$)$_m$, NR$^{11}$ and O(CR$^9$R$^{10}$)$_m$, wherein m is an integer selected from 1 to 3, wherein when A is N, X is (CH$_2$)$_m$. More preferably, X is (CH$_2$)$_m$, wherein m is 1 or 2.

$R^{11}$ is preferably selected from H, $C_1$–$C_{10}$ alkyl substituted with 0–2 $R^7$, $C_1$–$C_{10}$ fluoroalkyl substituted with 0–2 $R^7$, $C_2$–$C_1$o alkenyl substituted with 0–2 $R^7$, $C_2$–$C_{10}$ fluoroalkenyl substituted with 0–2 $R^7$, aryl substituted with 0–2 $R^7$ and fluroaryl substituted with 0–2 $R^7$.

Thus, preferred tripodal polyaminophosphonate chelants according to the present invention have the formula:

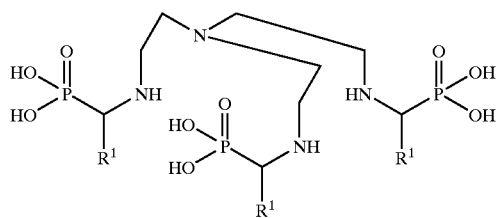

wherein $R^1$ is selected from phenyl, benzyl, imidazolyl, pyridyl and thiophenyl, each substituted with 0–2 OH. A particularly preferred tripodal polyaminophosphonate chelant has the formula:

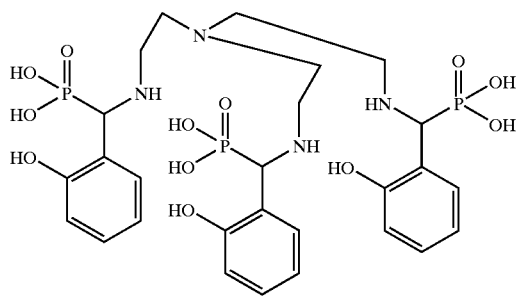

Among preferred tripodal polyaminophosphonate chelants are chelants in which the phosphorous atoms include $^{32}$P.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^9$) occurs more than one time in any constituent or formula for a compound, its definition at each occurrence is independent of its definition at every other occurrence. Thus, for example, if a group is shown to be substituted with 0–2 $R^9$, then said group may optionally be substituted with up to two $R^9$ groups and $R^9$ at each occurrence is selected independently from the definition of $R^9$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

A "diagnostic kit" or "kit" comprises a collection of components, termed the formulation, in one or more vials which are used by the practicing end user in a clinical or pharmacy setting to synthesize diagnostic radiopharmaceuticals. The kit provides all the requisite components to synthesize and use the diagnostic radiopharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes and shielding, and imaging equipment.

Buffers useful in the preparation of metallopharmaceuticals and in diagnostic kits for the preparation of said radiopharmaceuticals include but are not limited to phosphate, citrate, sulfosalicylate, and acetate. A more com-plete list can be found in the United States Pharmacopeia.

A "transfer ligand" is a ligand that forms an intermediate complex with a metal ion that is stable enough to prevent unwanted side-reactions but labile enough to be converted to a metallopharmaceutical. The formation of the intermediate complex is kinetically favored while the formation of the metallopharmaceutical is thermodynamically favored. Transfer ligands useful in the preparation of metallopharmaceuticals and in diagnostic kits useful for the preparation of diagnostic radiopharmaceuticals include but are not limited to gluconate, glucoheptonate, mannitol, glucarate, N,N, N',N'-ethylenediaminetetraacetic acid, pyrophosphate and methylenediphosphonate. In general, transfer ligands are comprised of oxygen or nitrogen donor atoms.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include but are not limited to stannous chloride, stannous fluoride, formamidine sulfinic acid, ascorbic acid, cysteine, phosphines, and cuprous or ferrous salts. Other reducing agents are described in Brodack et. al., PCT Application 94/22496, which is incorporated herein by reference.

The phrase "pharmaceutically acceptable" is employed herein to refer to those compounds, materials, compositions, and/or dosage forms which are, within the scope of sound medical judgment, suitable for use in contact with the tis-sues of human beings and animals without excessive toxicity, irritation, allergic response, or other problem or compli-cation, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc . . . ) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The coordination sphere of the radionuclide includes all the ligands or groups bound to the radionuclide. For a metallic radionuclide to be stable it typically has a coordination number (number of donor atoms) comprised of an integer greater than or equal to 4 and less than or equal to 9; that is there are 4 to 9 atoms bound to the metal and it is said to have a complete coordination sphere. The requisite coordination number for a stable radionuclide complex is determined by the identity of the radionuclide, its oxidation state, and the type of donor atoms. If the chelant does not provide all of the atoms necessary to stabilize the metal radionuclide by completing its coordination sphere, the coordination sphere is completed by donor atoms from other ligands, termed ancillary or co-ligands, which can also be either terminal or chelating.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits for the preparation of radiopharmaceuticals include but are not limited to etha-nol, glycerin, polyethylene glycol, propylene glycol, polyoxyethylene sorbitan monooleate, sorbitan monooleate, poly-sorbates, poly(oxyethylene)poly(oxypropylene)poly(oxyethyl-ene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chlorbutanol, and methyl, propyl or butyl paraben.

The technetium and rhenium radiopharmaceuticals of the present invention can be easily prepared by admixing a salt of a radionuclide, a compound of the present invention, and a reducing agent, in an aqueous solution at temperatures from 0 to 100° C. The technetium and rhenium radionuclides are preferably in the chemical form of pertechnetate or perrhenate and a pharmaceutically acceptable cation. The pertechnetate salt form is preferably sodium pertechnetate such as obtained from commercial Tc-99m generators. The amount of pertechnetate used to prepare the radiopharmaceuticals of the present invention can range from 0.1 mCi to 1 Ci, or more preferably from 1 to 200 mCi.

The amount of the compounds of the present invention used to prepare the technetium and rhenium radiopharmaceuticals of the present invention can range from 0.01 $\mu$g to 10 mg, or more preferably from 0.5 $\mu$g to 200 $\mu$g. The amount used will be dictated by the amounts of the other reactants and the identity of the radiopharmaceuticals of the present invention to be prepared.

The metallopharmaceuticals of the present invention comprised of a metal of atomic number 21–31, 39–43, 44–50, 56–74, 76–80, 82–83, and 90 can be easily prepared by admixing a salt of a radionuclide and a reagent of the present invention, in an aqueous solution at temperatures from 0 to 100° C. These metals (radioisotopes, paramagnetic metals, and X-ray absorbing metals) are typically obtained as a dilute aqueous solution in a mineral acid, such as hydrochloric, nitric or sulfuric acid. The metals are combined with from one to about one thousand equivalents of the reagents of the present invention dissolved in aqueous solution. A buffer is typically used to maintain the pH of the reaction mixture between 3 and 10.

The total time of preparation will vary depending on the identity of the metal ion, the identities and amounts of the reactants and the procedure used for the preparation. The preparations may be complete, resulting in >80% yield of the metallopharmaceutical, in 1 minute or may require more time. If higher purity metallopharmaceuticals are needed or desired, the products can be purified by any of a number of techniques well known to those skilled in the art such as liquid chromatography, solid phase extraction, solvent extraction, dialysis or ultrafiltration.

Synthesis of Tripodal Polyaminophosphonate Chelants

The present invention provides a new class of tripodal polyaminophosphonate chelants that can rapidly form highly stable metal chelates useful as diagnostic or therapeutic metalloradiopharmaceuticals, or magnetic resonance imaging contrast agents, or X-ray or CT contrast agents. In general, the tripodal polyaminophosphonate chelants are composed of two parts: a spacer providing the 3-D chelant framework and chelating arms for metal chelation. The spacer A can be built on a single bridging moiety selected from: $R^1$—C, $R^1$—Si, $R^1$—Ge, N, P, P($=$O), or a cyclic group such as 1,3,5-substituted cyclohexane. The spacer A is used in such a way that all three chelating arms are properly arranged in the right conformation for metal chelation. The chelating groups are not just limited to carboxylates and may contain groups such as phosphonate, phosphinate, hydroxymate, hydroxylethyl, and hydroxyaryl.

The tripodal triamine A(X—NH$_2$)$_3$ is an important intermediate. Examples of A(X—NH$_2$)$_3$ are shown in Chart I. Most of these tripodal amines are either commercially available or can be readily prepared according to the literature methods. For example, tris(2-aminoethyl)amine and tris(3-aminopropyl)amine are available from Aldrich. 1,1,1-Tris(aminomethyl)ethane (TAME) and 1,2,3-triaminopropane can be prepared according to the procedure by Liu, et al (*Inorg. Chem.* 1993, 32, 4268–4276 and *Inorg. Chem.* 1993, 32, 1756–1783); 1,3,5-triaminocyclohexane by Bowen, T. et al (*Bioorg. & Med. Chem. Lett.* 1996, 6, 807–810); tris-endo-tricyclo-[5.2.1.0$^{4,10}$]decane-2,5,8-triamine by Aguilera, A. et al (*Synthetic Commun.* 1991, 21, 1643–1648); 2,2-bis(aminomethyl)-1,3-propanediamine by McAuley, A. et al (*Can. J. Chem.* 1989, 67, 1650–1656); 1,3,5-triamino-1,3,5-trideoxy-cis-inositol by Ghislett, M. et al (*Helv. Chim. Acta* 1992, 75, 2233–2251); germanium tetrahydrazide by Singh, P. R. et al (*Nucl. Med. Biol.* 1994, 21, 1115–1118); and trihydrazidophosphine oxide by Corlij, M. et al (*J. Nucl. Biol. Med.* 1992, 36, 296–300).

Chart I. Examples of Tripodal Triamines.

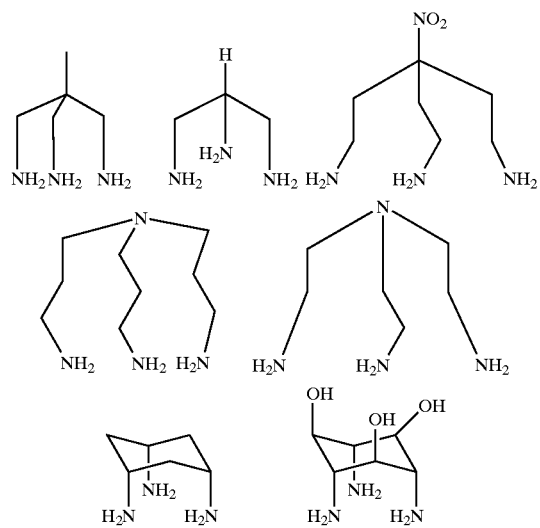

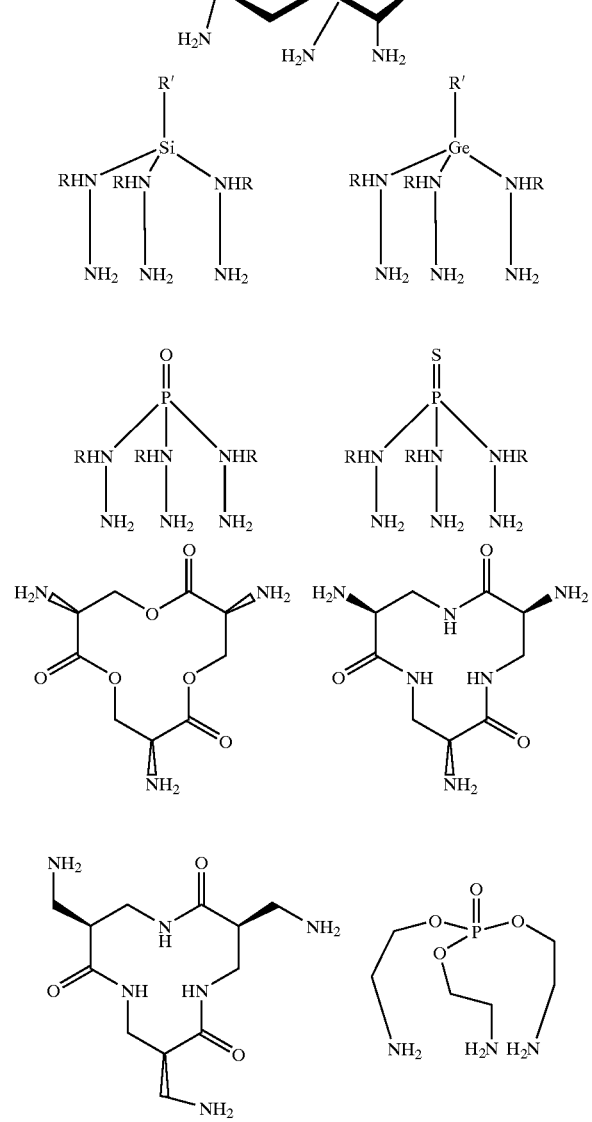

Once the tripodal triamine intermediate is available, synthesis of the tripodal polyaminophosphonate chelant is straightforward. In general, the triamine is allowed to react with three equivalents of aldehyde or ketone to form the corresponding Schiff base (Chart II). The Schiff base contains the imine C$=$N bonds, which can be reduced with a variety of reducing agents to produce the corresponding amine (CH—NH) bonds. Diethylphosphite is as known reducing agent. In this invention, diethylphosphite was used for reductive addition of C$=$N bonds using tetramethylguanidine as a catalyst according to the literature method (*Tetrahedron letters* 1998, 39, 7615–7618). The resulting product is diethyl aminophosphinate, which can be readily hydrolyzed to give the corresponding aminophosphonic acid.

Chart II. Synthesis of Tripodal Polyaminophosphonic Acid.

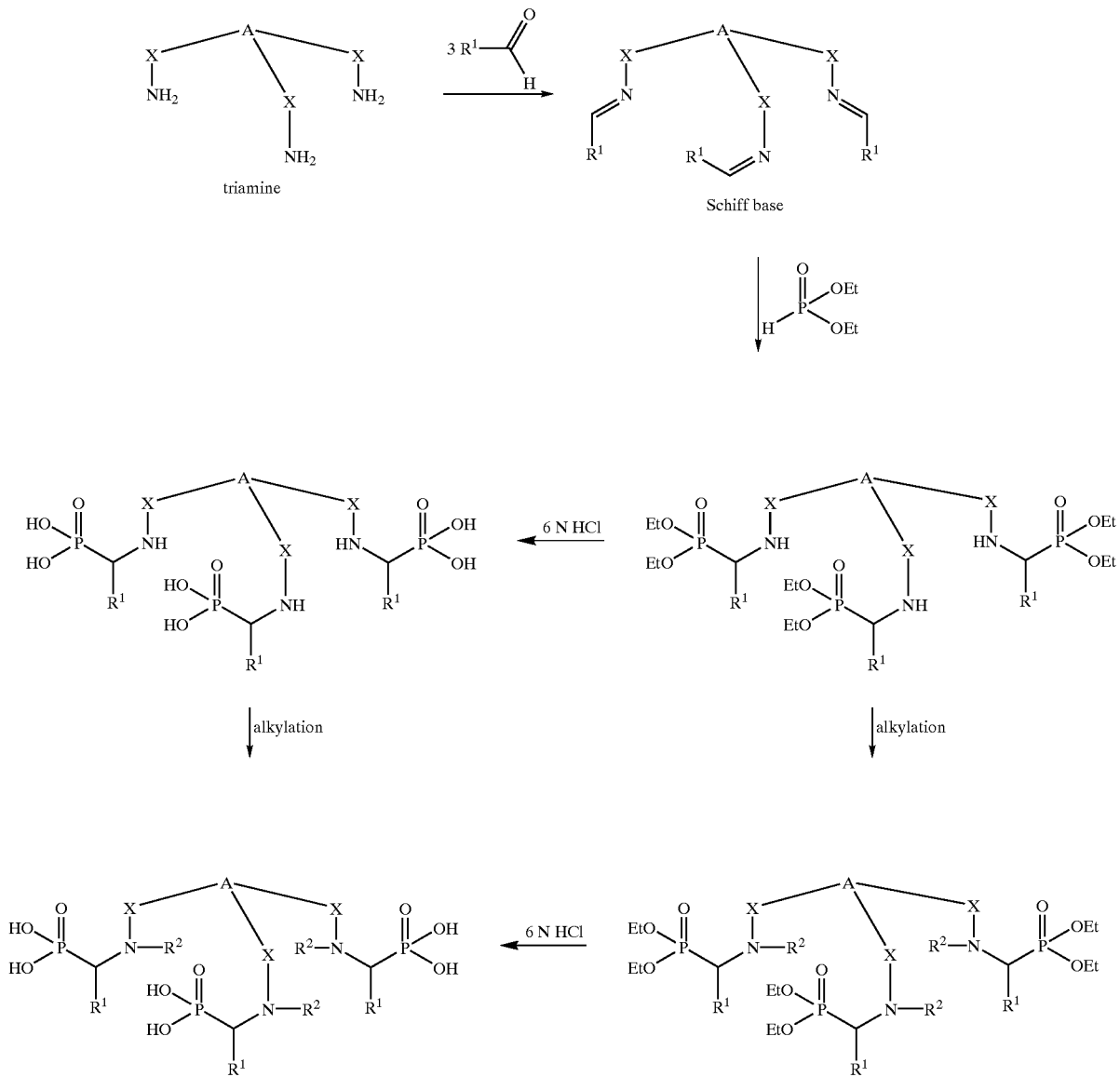

The secondary amine group (Chart II) in the tripodal polyaminophosphonate chelant can be further functionalized by alkylation of the amine-N atoms to give the corresponding functionalized tripodal polyaminophosphonate chelant.

EXAMPLES

Instruments. $^1$H NMR spectra were recorded on a 270 MHz Bruker spectrometer. The $^1$H and $^{13}$C NMR data were reported as □ (ppm) relative to TMS. Electrospray MS analyses were performed using a VG Quattro mass spectrometer. LC-MS spectra were collected using a HP1100 LC/MSD system with API-electrospray interface. The high-performance liquid HPLC methods used a Hewlett Packard Model 1090 instrument with radiometric detector using a sodium iodide probe. The ITLC method used Gelman Sciences ITLC paper strip, and a mixture of acetone and saline (50:50=v:v) as the mobile phase. Using this method, the metal chelate migrate to the solvent front while the "metal colloid" and free metal ion remain at the origin.

Diethylphosphite, tetramethylguanidine (TMG), and tris (2-aminoethyl)amine (tren) were purchased from Aldrich Chemical Co., and were used without further purification. Tris((2-(salicylalideneamino)ethyl)amine)($H_3$saltren) was prepared according to the literature method (Liu, S., et al. *J. Am. Chem. Soc.* 1992, 114, 6081–6087).

Example I

Synthesis of tris(2-aminoethyl)amine-N,N',N''-tris (2-hydroxybenzyl)methylenephosphonic acid (Tren (HBP)$_3$).

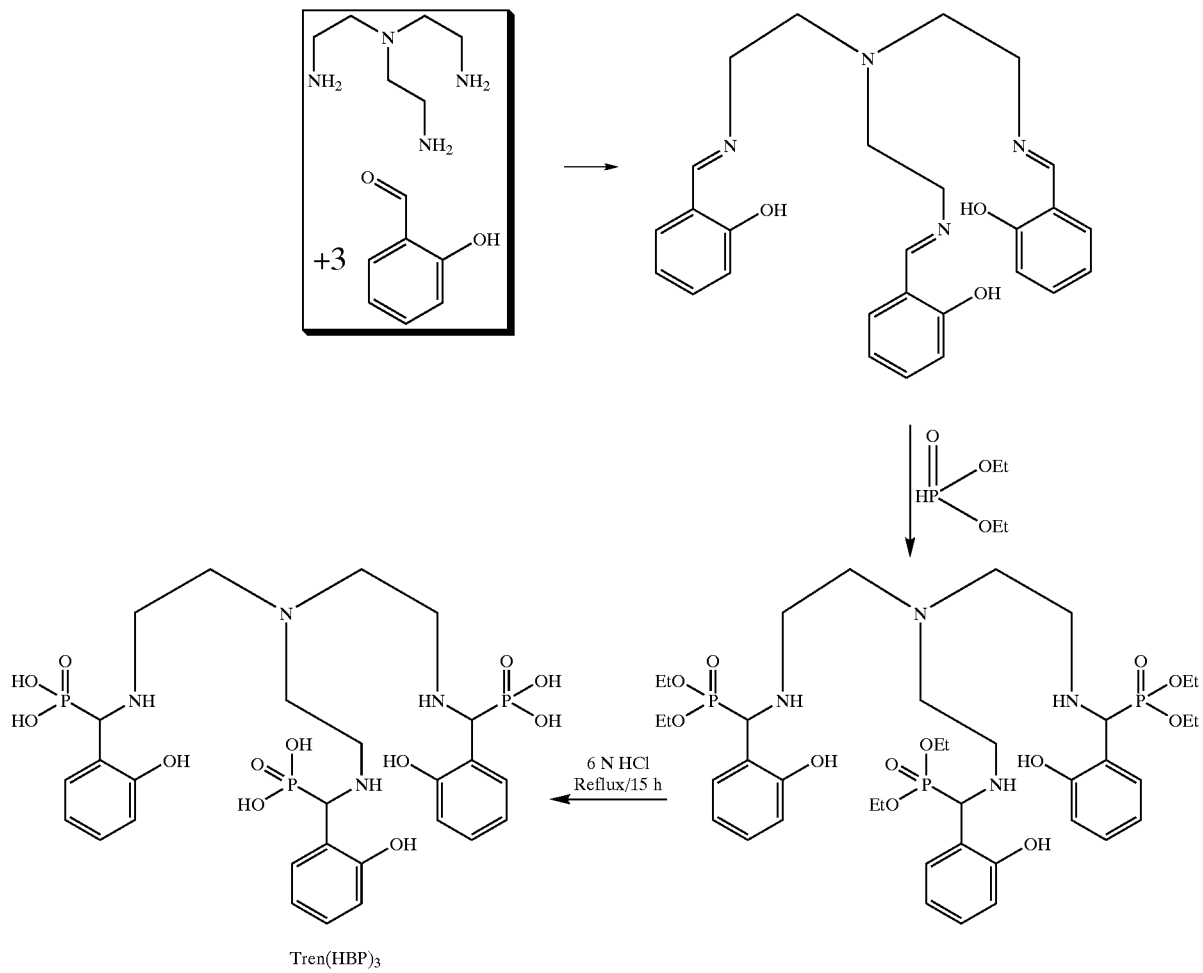

Tren(HBP)$_3$

To a bright yellow solution of H$_3$saltren (0.92 g, 2.0 mmol) in diethylphosphite (15.0 mL) was added tetramethyl-guanidine (TMG, 0.3 mL). The bright yellow color slowly disappeared (~2 hr) upon stirring at room temperature, indication that the Schiff based was completely reduced. Excess diethylphosphite was removed to give a gummy liquid. The residue was dissolved in 6 N HCl (25 mL) and the mixture was heated to reflux overnight (15 hr). The resulting solution was cooled to room temperature, and the pH was adjusted to about 2 to give a pink solid. The solid was isolated by filtration, washed with water, and methanol, and dried under vacuum.

The crude product was dissolved in minimum amount of 5 NaOH solution to give a brownish color. The pH was then adjusted to ~2 using the concentrated HCl. The mixture was heated to reflux and the pink solid was filtered, washed with methanol and dried under vacuum overnight. The filtrate was cooled to room temperature to give a white precipitate. The solid was collected by filtration, washed with methanol and dried under vacuum overnight. ES-MS (negative mode): m/e=726.8 for [M+Na-H]$^+$ (M=C$_{27}$H$_{39}$N$_4$O$_{12}$P$_3$); 363.2 for [M−2H]$^{2-}$. $^1$H NMR (in D$_2$O+KOD): 7.25 (m, 3H, aromatic); 6.93 (t, 3H, aromatic); 6.46 (m, 6H, aromatic); 4.08 (dd, 3H, Ph—CH); and 2.2–2.4 (m, 12H, CH$_2$CH$_2$). $^{31}$P NMR (in D$_2$O+KOD): 18.6 ppm (relative to phosphoric acid).

Example II

Synthesis of In-111 Complex of Tren(HBP)$_3$

To a clean 5 mL vial containing 0.5 mL of the Tren(HBP)$_3$ solution (4 mg/mL in 0.5 M NH$_4$OAc, pH=7.5) was added 10 □L of $^{111}$InCl$_3$ solution (~1 mCi) in 0.05 N HCl. The reaction mixture was heated at 80° C. for 15 min. After cooling to room temperature, a sample of the resulting solution was analyzed by ITLC. The yield was 98%.

Example III

Synthesis of Y-90 Complex of Tren(HBP)$_3$

To a clean 5 mL vial containing 0.5 mL of the Tren(HBP)$_3$ solution (4 mg/mL in 0.5 M NH$_4$OAc, pH=7.5) was added 15 □L of $^{90}$YCl$_3$ solution (~10 mCi) in 0.05 N HCl. The reaction mixture was heated at 80° C. for 15 min. After cooling to room temperature, the resulting solution was analyzed by ITLC. The yield was 97%.

Example IV

Synthesis of Lu-177 Complex of Tren(HBP)$_3$

To a clean 5 mL vial containing 0.5 mL of the Tren(HBP)$_3$ solution (4 mg/mL in 0.5 M NH$_4$OAc, pH =7.5) was added 10 μL of $^{177}$LuCl$_3$ solution (~5 mCi) in 0.05 N HCl. The reaction mixture was heated at 80° C. for 15 min. After cooling to room temperature, the resulting solution was analyzed by ITLC. The yield was 95%.

Utility

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Pat. Nos. 5,155,215; 5,087,440; Margerstadt et al., *Magn. Reson. Med.,* 1986, 3, 808; Runge et al., *Radiology,* 1988, 166, 835; and Bousquet et al., *Radiology* 1988, 166, 693. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

Other features of the invention will become apparent in the course of the following descriptions of exemplary embodiments which are given for illustration of the invention and are not intended to be limiting thereof.

This invention relates particularly to the use of the new metal chelates as contrast agents for x-ray and MRI imaging. This invention also relates to the use of radiolanthanide metal chelates particularly useful as therapeutic radiopharmaceuticals for bone pain relief, bone marrow suppression, the treatment of bone cancer, and various bone disorders.

The radiopharmaceuticals of the present invention comprised of a gamma emitting isotope are useful for diagnosis of bone metastases, bone disorders, myocardial infarction, infarctions of the spleen and bowel, inflammatory bowel disease, radiation injury, as well as metastastic calcification.

The radiopharmaceuticals of the present invention comprised of a beta, alpha or Auger electron emitting isotope are useful for bone pain relief, bone marrow suppression, the treatment of bone cancer, and various bone disorders, by delivering a cytotoxic dose of radiation to the locus of the disease tissues.

The compounds of the present invention comprised of one or more paramagnetic metal ions selected from gadolinium, dysprosium, iron, and manganese, are useful as contrast agents for magnetic resonance imaging (MRI) of bone metastases, bone disorders, myocardial infarction, infarctions of the spleen and bowel, inflammatory bowel disease, radiation injury, as well as metastastic calcification.

The compounds of the present invention comprised of one or more heavy atoms with atomic number of 20 or greater are useful as X-ray contrast agents for X-ray imaging bone metastases, bone disorders, myocardial infarction, infarctions of the spleen and bowel, inflammatory bowel disease, radiation injury, as well as metastastic calcification.

Biodistribution Study in Rats

Biodistribution of the radiopharmaceuticals was performed according to the literature methods (Goeckeler et al. *J. Nucl. Med.* 1987, 28, 495–504). Briefly, twenty to one hundred microliters of the radiopharmaceutical solution were injected to the tail veins of unanesthetized Sprague Dawley rats (160–200 g) and each rat was housed individually in a cage for 2 h. At 2 h postinjection the animals were scarified. One mililiter samples of blood were taken by cardiac puncture and weighed. The whole animals were then weighed and dissected. The excised tissues were washed with saline, blotted, and weighed prior to counting. Cage droppings and kill papers were collected and counted with the bladder to quantify the urine activity. One femur was excised and dissected free of soft tissues before weighing and counting. All tissues remaining after the dissection were counted and marked as carcass. The data is collected in terms of the percentage of the injected radioactivity per gram (%ID/g) of each specified type and bone/tissue ratio of injected radioactivity.

For gamma scintigraphic imaging, 50–100 μCi of the radiopharmaceutical were injected to the tail veins of unanesthetized Sprague Dawley rats (160–200 g). Serial images were collected for 2 hours with a 256×256 matrix, no zoom, 5 minute dynamic images. A known source is placed in the image field (20–90 μCi) to evaluate region of interest (ROI) uptake. Images were also acquired 24 hours post injection to determine retention of the compound in the tissues. The uptake is determined by taking the fraction of the total counts in an inscribed area for ROI/source and multiplying the known μCi. The result is μCi for the ROI. The data is collected in terms of the percentage of the injected radioactivity (%ID) of each specified organ or tissue.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tissues and counting the amount of radioactivity present by standard techniques.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the tumors. The effectiveness of the contrast agents can be readily seen by comparison to the images obtain from animals that are not administered a contrast agent.

Obviously, numerous modifications and variations of the present invention are possible in light of the above teachings. It is therefore to be understood that within the scope of the appended claims, the invention may be practiced otherwise that as specifically described herein.

What is claimed is:

1. A tripodal polyaminophosphonate chelant having the formula:

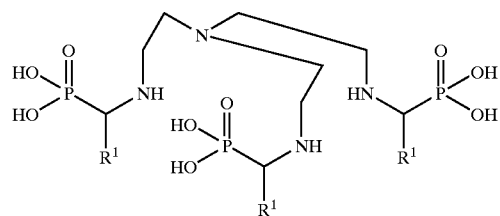

wherein $R^1$ is selected from the group consisting of phenyl, benzyl, imidazolyl, pyridyl and thiophenyl, each substituted with 0–2 OH.

2. A tripodal polyaminophosphonate chelant according to claim 1, having the formula:

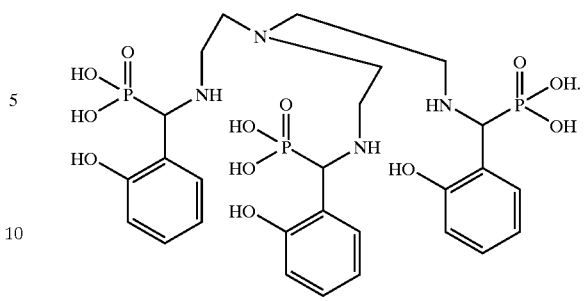

3. A pharmaceutical composition for treating heavy metal toxicity in a patient in need thereof, comprising a therapeutically effective amount of the tripodal polyaminophosphonate chelant of claim 1 and a pharmaceutically acceptable carrier.

* * * * *